United States Patent [19]

Stoy et al.

[11] 4,026,296
[45] May 31, 1977

[54] HYDROPHILIC SURGICAL TUBULAR DEVICE

[75] Inventors: Artur Stoy; Vladimír Stoy; Jiří Zima, all of Prague, Czechoslovakia

[73] Assignee: Ceskoslovenska akademie ved, Prague, Czechoslovakia

[22] Filed: Mar. 3, 1975

[21] Appl. No.: 554,625

[30] Foreign Application Priority Data
Mar. 19, 1974 Czechoslovakia .................. 1981/74

[52] U.S. Cl. ............................ 128/349 B; 128/351
[51] Int. Cl.² ........................................ A61M 25/00
[58] Field of Search ........................ 128/348–351, 128/334, 343; 3/1

[56] References Cited
UNITED STATES PATENTS

| | | | |
|---|---|---|---|
| 3,566,874 | 3/1971 | Shepherd et al. ............... | 128/349 R |
| 3,625,741 | 12/1971 | Stoy et al. ...................... | 128/349 X |
| 3,931,123 | 1/1976 | Vacik et al. ..................... | 3/1 X |

OTHER PUBLICATIONS

Isacoff — Polyacrylates in Cosmetics — Cosmetics & Perfumery, vol. 88, Feb. 1973, pp. 35–37.

*Primary Examiner*—Dalton L. Truluck

[57] ABSTRACT

The invention relates to surgical tubular devices, such as catheters, tracheal or gastric intubation or sounding tubes, tubes for removal of tracheal or pulmonary secretions, and cyctoscopes designed to be temporarily introduced into cavities of living body and consisting of entirely or partially of a hydrophilic copolymer of acrylonitrile with either acrylamide or acrylic acid and, if desired, with a small amount of other co-monomers. The copolymers are swellable in water and aqueous solutions. In the swelled condition they are pliable, elastic and strong. Their properties can be changed by changing the degree of hydrolysis, if the copolymer was prepared by partial hydrolysis of polyacrylonitrile, or by changing the content of hydrophilic units, if the copolymer was obtained by copolymerization of a monomer mixture.

The outer layer or surface layer of the part to be introduced into the cavities of living body such as the larynx, trachea, urethra, etc., contains neutralized anions in side-substituents such as carboxylic, sulphonic, sulphuric or phosphoric groups attached to the copolymer main chain by covalent bonds. The part expected to be exposed to the atmosphere during the application to the patient is permanently protected against drying by a layer of a polymer or copolymer impermeable for water and water vapors.

6 Claims, 6 Drawing Figures

HYDROPHILIC SURGICAL TUBULAR DEVICE

BACKGROUND OF THE INVENTION

1. Field of the Invention

The present invention relates to surgical tubular device designed to be temporarily introduced into cavities of living body, such as a catheter, tracheal or gastric intubation or sounding tube, cystoscope and the like, and a method of manufacturing same.

2. Description of the Prior art

Until now, surgical tubular devices designed to be temporarily introduced into cavities of the living body have been manufactured from rubber or from highly plasticized polyvinylchloride, or from other similar hydrophobic polymers impermeable for water and aqueous solutes. Such polymers are very different, from the physical standpoint, from living tissues. Their surface has a comparatively high coefficient of friction with respect to mucous membranes; thus, surgical devices used hitherto often hurt the tissues. To avoid this, they often have to be lubricated before use. Infection hazard is thereby increased.

Hydrophobic catheters, intubation sounds and the like cannot absorb drugs which would then gradually diffuse into the surrounding mucous membrane. It was therefore suggested to provide such hydrophobic tubular devices with a thin layer of sparingly cross-linked glycol methacrylate polymer having a water sorbtion usually about 40% by weight, and thus capable to absorb water-soluble drugs. The main drawback of such coatings is that an intermediate layer must be formed first on which the hydrogel is laid by cross-linking polymerization of a monomer mixture. The intermediate layer has a swelling capacity lower than the outer hydrogel layer and simultaneously a good adhesion to rubber of plasticized PVC, otherwise the hydrogel layer would easily separate. The tenacity and elasticity of cross-linked ethyleneglycol methacrylate polymers is comparatively low and their layer must not be too thick. Thereby the ability to incorporate a sufficient amount of drugs is rather limited.

It has been already suggested to manufacture plain tubes from swelled copolymers of acrylonitrile with acrylamide, said tubes being provided with highly slippery surface layer. Simple tubes of this kind cannot be, however, directly used as intubation or sounding tubes or catheters because of its surface slipperyness and lack of strength, but can form rather a starting raw material for the surgical tubular device of the invention.

SUMMARY OF THE INVENTION

The invention relates to surgical tubular devices designed to be temporarily introduced into cavities of living body such as catheters, tracheal or gastric intubation or sounding tubes, tubes for removal of tracheal or pulmonary secretions, cyctoscopes and the like, consisting entirely or partially of a hydrophilic copolymer of acrylonitrile with either acrylamide or acrylic acid and, if desired, with a small amount of other comonomers. The copolymers are swellable in water and aqueous solutions; In swelled condition they are pliable, elastic and strong. Their properties can be changed by changing the degree of hydrolysis, if the copolymer was prepared by partial hydrolysis of polyacrylonitrile, or by changing the content of hydrophilic units, if the copolymer was obtained by copolymerization of a monomer mixture. At lower degrees of hydrolysis, or with lower content of hydrophilic units, the copolymers can be oriented by stretching, keeping in oriented state a comparatively high elasticity. At a higher content of hydrophilic units they are rubbery and contain up to about 85% of water at swelling equilibrium.

The outer layer or surface layer of the part to be introduced into the cavities of living body such as into larynx, trachea, urethra, etc., contains neutralized anions in side-substituents such as carboxylic, sulphonic, sulphuric or phosphoric groups attached to the copolymer main chain by covalent bonds. The part expected to be exposed to the atmosphere during the application to the patient is permanently protected against drying by a layer of a polymer or copolymer impermeable for water and water vapors.

The water swelled hydrogel can serve also to sustain release of appropriate drugs which can be absorbed therein prior to or during the storage.

BRIEF DESCRIPTION OF THE DRAWINGS

In the accompanying drawing

DESCRIPTION OF THE PREFERRED EMBODIMENTS

Figure 1:
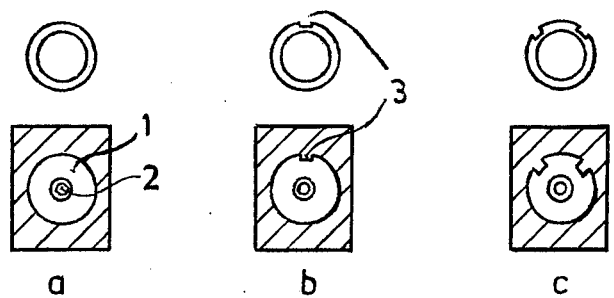
FIG. 1 illustrates diagrammatically three different cross-sections of the hydrogel main tube, together with cross-sections of the corresponding extrusion dies.

It has been found that faultless function of such devices can be secured only if the part which is exposed to the atmosphere during the application to a patient is protected against drying as well as against slipping into the cavities of a living body. The hydrophobic layer prevents the protected part from getting shrunk and brittle by drying out. As a result, the hydrogel tube remains elastic and pliable in its whole length and can be easily joined with necessary supplementing parts such as funnels, syringes, metering pumps and outlets of containers, by slipping its end on a fitting. As hydrophobic protecting layer natural or synthetic rubber can be applied using a self vulcanizing latex in which the respective part of the tubular device is dipped. Alternatively, an insulating sleeving from silicone or other rubber can be slipped onto the hydrogel tube. The assembly is easy if the sleeve is first swelled in a volatile liquid such as benzene or toluene. After evaporating of the swelling liquid the sleeve shrinks to its previous inside diameter and adheres by its high elasticity firmly to the hydrogel tube.

The part of the tubular device designed to be introduced into a cavity of a living body is made slippery by a suitable chemical treatment, forming anionic side groups covalently bonded with the copolymer. As anionic groups particularly carboxylic, sulphonic, sulphuric and phosphoric acid groups are suitable, neutralized with physiologically innocuous cations such as sodium, potassium or lithium cations. The treatment affects but a thin surface layer which is thereby made extremely slippery, the main part of the cross-section of the tube remaining unchanged.

Suitable chemical agents are e.g. aqueous solutions of alkali metal hydroxides causing saponification of nitrile and amide groups to carboxyls, or mixtures of concentrated sulphuric acid with glycerol or other soluble polyol, or vapors of chlorosulphonic acid or sulphur trioxide. Groups of phosphoric acid can be also introduced using known methods.

The shape of the surgical devices of this invention does not substantially differ from that of the known devices made from rubber or plasticized PVC. The end is free of sharp edges, preferably rounded, with either axial or side opening. Any even complicated form can be made using special extrusion dies and inflatable pockets from highly elastic hydrogels based on copolymers of acrylonitrile with acrylamide or acrylic acid. Inflatable pockets form part of thin hydrogel tubes slid on the tubular device and partially cemented thereto.

The copolymers from which the hydrophilic part of the device is made should contain not more than 80 molar percent of acrylonitrile units and preferably 40 to 65 molar percent, otherwise the desired character of elastic hydrogels could not be achieved. The minimum content of acrylonitrile units is determined by requirements concerning physical parameters such as toughness, elasticity, modulus, swelling capacity etc. These parameters depend on the density of the non-covalent network formed by polyacrylonitrile domains within the water-swelled amorphous hydrophilic chains consisting of acrylamide or acrylic acid units. Thus, if a random copolymer is used, the molar portion of acrylonitrile units should be higher than in case of a block copolymer whose undivided long polyacrylonitrile segments have a better opportunity to form crystalline domains than the same number of acrylonitrile units dispersed randomly along the chains. Although block copolymers of this kind are shape-retaining even if the molar portion of acrylonitrile units is very low, the swelling capacity in water exceeding 95% by weight, it is advisable to keep the content of acrylonitrile units higher than about 20% /molar/ and the swelling capacity in water lower than about 80% /weight/, in order to maintain the strength and pliability within reasonable limits.

Best results are obtained if the copolymer used is a multi-block copolymer containing in each macromolecule several sequences of acrylonitrile units alternating with sequences of acrylamide units. Such multi-block copolymers can be obtained by homogeneous acid hydrolysis of polyacrylonitrile plasticized by or dissolved in acidic solvents of polyacrylonitrile having a negligible chain transfer constant. The gels or solutions are first exposed to temperatures at which first acrylamide units are formed on the polyacrylonitrile chains, e.g. in case of concentrated nitric acid to temperatures above 20° C. Then the temperature is decreased so that no further isolated acrylamide groups are formed, the hydrolysis spreading from the acrylamide units already formed by the "zipper mechanism". Strong mineral acids can be used as solvents and simultaneously hydrolytic agents, e.g. concentrated nitric or phosphoric acid, or slightly diluted sulphuric acid. Sulphuric acid is a very strong hydrolytic agent but nitric acid is a better solvent. Thus, it is advantageous to use concentrated nitric acid as solvent and to add a small amount of sulphuric acid to the solution. Polyacrylonitrile in the form of a fine powder can be dispersed in nitric acid at temperatures below −20° C at which the rate of swelling is low, and then the temperature is slowly increased while stirring so that the dispersion is gradually transformed to a viscous homogeneous solution. If acrylonitrile homopolymer is used, the solution is briefly heated up to about 30°–40° C to initiate the zipper hydrolysis, and then left standing at 0°–20° C until the desired degree of hydrolysis is reached. The lower the temperature, the longer the sequences or "blocks" in the copolymer. The necessary time increases, however, with decreasing temperature.

Best results are obtained if the steps of the hydrolysis are distinctly separated. Similarly, if acrylonitrile is polymerized directly in an acidic solvent such as in nitric acid or in an aqueous zinc chloride or lithium bromide containing solution, the step of partial hydrolysis should be distinctly separated form the step of polymerization. This can be achieved e.g. by polymerizing acrylonitrile in concentrated nitric acid at low temperatures, using a suitable redox initiator. After finished polymerization the rate of hydrolysis is increased either by adding sulphuric acid, or by increasing temperature, and then decreasing it again as mentioned above. If the polymerization is carried out in concentrated aqueous solutions containing zinc chloride, lithium bromide or other salts capable of dissolving polyacrylonitrile, the rate of hydrolysis may be increased best by dissolving hydrogen halide in the polymer solution, or in the solvent-plasticized gel respectively. This method can be performed advantageously in such a way that a viscous solution of polyacrylonitrile in one of the above mentioned salt solutions is extruded into a coagulating bath in which the tube is but partially coagulated. The tube is then left standing for several hours until the salts are evenly distributed by diffusion so that a rubbery gel containing from about 20 to about 40% of polyacrylonitrile is obtained. The gel can be then partially hydrolyzed either by increasing the temperature to about 70° to about 120° C, or better by treating it with gaseous hydrogen halide at −20° to about 30° C until the desired degree of hydrolysis is achieved. The salts are then washed out and the hydrogen halide neutralized, in case of zinc chloride containing solvent preferably with a diluted aqueous solution of a substance yielding anions forming insoluble zinc compounds. Such anions are contained in solutions of carbonates, bicarbonates, chromates, phosphates, hydroxides and others.

Although acrylamide is preferred as the hydrophilic component, especially if formed by controlled partial acid hydrolysis mentioned above, it is possible to use also other hydrophilic components such as acrylic acid, methacrylamide, methacrylic acid, sodium ethylene sulphonate, sodium styrene sulphonate, maleine anhydride, itaconic acid or other mono-olefinic acids capable to copolymerize with acrylonitrile. N-alkyl- or N-hydroxyalkyl amides of acrylic and methacrylic acid can be also used. Hydrophilic co-monomers can be incorporated in such an amount that the partial hydrolysis can be dispensed with.

Best results are obtained if the amount of co-monomer units in the starting copolymer prior to partial hydrolysis is lower than about 10 mol. percent, preferably lower than about 2%. Besides the hydrophilic co-monomers mentioned in the preceding paragraph, also hydrophobic co-monomers can be employed such as lower alkyl esters of acrylic and methacrylic acids, vinyl pyridine, vinyl carbazole, styrene, alpha-methyl styrene, alpha-chlor styrene, or vinyl pyrrolidone.

It is also possible to polymerize acrylonitrile under crosslinking conditions in acidic solvents having a negligible chain transfer constant, either by adding a small amount of a suitable crosslinking agent such as ethylene glycol dimethacrylate or N,N-methylene bismethacrylamide, or by carrying out the polymerization at such a high monomer concentration that chain transfer onto the monomer causes crosslinking. The polymerization is then to be carried out in a mold because crosslinked gels cannot be shaped. A lyogel elastic tube is obtained, consisting of polyacrylonitrile plasticized with e.g. nitric acid or aqueous zinc chloride solution. Partial hydrolysis is then carried out in the above described manner.

Simple sounding tubes designed e.g. for taking samples of gastric juice or for removal of secretions can be made from tubes having its end tip rounded by working in dry or half-dry state, or by pressing at increased temperatures in presence of a polyacrylonitrile solvent, the part to be exposed to atmosphere and being coated with a sufficiently elastic polymer such as rubber to prevent drying. The other part is made slippery by treating with strong alkali lyes or other chemical agents capable of forming anionic side groups on the copolymer chain. A side opening can be made with or without closing the original axial opening of the tube. The closing of the end to be inserted into the cavity of living body can be carried out in various ways, e.g. by cementing a shaped stopper from the same or similar hydrogel into the opening, or by shaping the end of the tube just leaving the extrusion die and not yet fully coagulated.

For cementing a shaped stopper into the end of the tube any polyacrylonitrile solvent can be used such as dimethyl formamide or dimethyl sulphoxide. The cementing is preferably carried out with both stopper and tube swelled with water, glycerol or similar, because dry hydrophilic polymers — xerogels — tend to spontaneous cracking in contact with the solvents.

According to another embodiment of the manufacturing process usual surgical tubular devices from rubber or plasticized PVC are coated with a layer of the above hydrophilic acrylonitrile copolymers either by dipping them into a copolymer solution and coagulating the latter e.g. in cold water, or by spraying or painting said copolymer solutions, also with subsequent coagulation, or better, by slipping a thin tube from said hydrophilic swelled copolymer onto said tubular device. The slipping of the tube onto the device is made easier if the thin hydrogel tube is previously swelled in a mixture of a polyacrylonitrile solvent with water, or by increasing temporarily the inside diameter of the thin tube by radial enlargement. In the first case the solvent of polyacrylonitrile is washed out and the outer tube shrinks; adhering firmly to the tubular device. In the other case the same effect is attained by immersing into hot water in which the radial orientation relaxes to the original inside diameter. The rounded end can be covered uniformly with the hydrophilic copolymer by molding the overlapping thin hydrogel tube in the presence of a solvent of polyacrylonitrile and removing the solvent by washing in water. It is also possible to prepare the thin hydrogel tube with the end closed at the extrusion die. The thin outer tube can cover the part to be inserted, the part to be exposed to atmosphere being left bare.

More complex surgical tubular devices provided with one or two coaxial channels for flushing out the urinary bladder with drug solutions, or provided with an inflatable pocket holding the tubular device in desired position, can be manufactured using suitable extrusion dies with more than one inlet for coagulating liquid so that coaxial channels are formed. Instead of such tubular channels coaxial grooves on the tube surface can be created using suitable extrusion dies such as shown in FIG. 1b and c of the accompanying drawing. The tube with grooves is covered by a thin hydrogel tube from the same or similar, highly elastic hydrogel. If the end of the tubular device is formed by dipping into a hydrogel solution and coagulating it, any part of the groove or grooves which has to remain free can be protected from filling with the hydrogel by a suitable water-soluble polymer such as carboxymethyl cellulose which is finally washed out. Another way to preserve the groove is to insert a wire or similar device which is pulled out after the finished treatment.

The upper hydrogel tube can be cemented to the main tube except the part forming an inflatable pocket which communicates with one end of the channel, the other end of the channel being formed with a suitable filling device provided with a check valve. The part forming the pocket can be previously coated with sodium salt of carboxymethyl cellulose or with another water-soluble polymer which is washed out after the remaining parts have been cemented together.

The inflatable pocket forming an integral part of the outer thin hydrogel tube possesses the advantage that the whole surface is entirely smooth. Physiologic saline with which the pocket is filled may contain drugs such as bacteriostatics, bactericides and anaesthetics which diffuse gradually through the inflated hydrogel membrane. The main tube can have a recess underneath the inflatable pocket, if desired.

The outer thin tube can be closed at one end before being slipped onto the main catheter tube, forming a slender sack so that the whole catheter including its tip is uniformly and smoothly covered with hydrogel. The necessary side-opening can be made before or after slipping the thin tube onto the main tube.

To avoid any dead space near the opening, the end of the closed catheter can be filled with a stopper cemented thereto or with a polymer solution coagulated afterwards.

If the main tube of the tubular device is made from rubber or similar hydrophobic material, it is sufficient to cover it with a thin hydrogel tube except for the part to be introduced into the body. Another possibility is to make the whole part to be introduced into the living body from the hydrogel, the part to be exposed to the atmosphere being made from rubber or similar. The two parts are joint by cementing together their ends adapted thereto.

The outer hydrogel thin tube can be cemented to the main tube at the ends only so that the whole space between them can be filled with physiologic saline solution containing, if desired, suitable drugs. Thereby the outer tube is pressed against the mucous membrane of e.g. the urethra, sealing it completely. The end protruding into the bladder is simultaneously inflated to prevent the catheter from slipping out.

The hydrophilic copolymer of acrylonitrile can be subsequently cross-linked, if desired. The catheter is then treated with a suitable cross-linking agent such as an aqueous acid formaldehyde solution, or a suitable diepoxide reacting with hydroxylic and amidic side groups, or with a di-isocyanate. The cross-linking with formaldehyde can be carried out also in an appropriate stage of washing when the gel contains still nitric or sulphuric acid. When using gaseous hydrogen halide to increase the rate of hydrolysis, gaseous formaldehyde can be admixed thereto. The crosslinking can be carried out either before imparting anionic groups to the surface layer, or thereafter.

If the catheter or similar device is sterilized with ethylene oxide, some hydrophilic groups $—O/CH_2CH_2O/_nH$ may be formed on the surface, decreasing also the coefficient of friction of the swelled hydrogel.

The hydrogels easily absorb various drugs, securing long term sterility and sustained release of drugs An important step in manufacturing surgical tubular devices is the shaping of the end tip to be introduced into the body. The end tip has to be quite smooth, suitably rounded and inseparably formed to the tube. There are several ways to form the ending. First of all it is possible to mold the extruded tube at the extrusion die where the tube is not yet fully coagulated, closing simultaneously the water inlet through an axial mandrel. Thereby the inside diameter is reduced to zero and a stick or a monofil is temporarily formed instead of a tube. In order to maintain the diameter constant the feed of the polymer solution can be simultaneously increased. After a short time interval the feed of water is renewed and that of the polymer solution reduced to the original value — compare FIGS. 4 and 5. The thick monofilament sections are then cut in the middle and so are the tube sections between them. The ends are rounded, preferably in a not entirely dry condition, by grinding. The ends can be also frozen before grinding. Another way is to mold the ends by heat and pressure in presence of a solvent of polyacrylonitrile.

Figure 6:
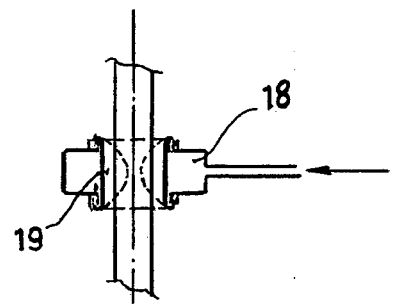
FIG. 6 shows diagrammatically, in an axial section, a tool for molding the just extruded, only superficially coagulated tube.

It is also possible to mold the extruded tube usiing a suitable tool instead of interrupting the inlet of the coagulating liquid by an axial mandrel. Such tool may be a sort of pliers, or a ring-like inflatable air tube constricting the extruded tube along a short path - see FIG. 6. The process can be automated.

Still another way to close the end of the tube is dipping the end into a viscous hydrogel solution and sucking the latter into the tube to the desired level. The tube is preferably inclined so as to obtain a bevelled bottom. The hydrogel solution is rapidly coagulated in water and the solvent washed out. Use of a hydrogel stopper has been already mentioned.

The end of the tubular device can be worked mechanically. Finally the surface is made slippery in wet condition by imparting anionic groups thereto.

Several methods for manufacturing surgical tubular devices of the invention are described in following non-limitative Examples. All parts and percentages are by weight if not stated otherwise.

EXAMPLE 1

Polyacrylonitrile with average degree of polymerization 4500, prepared by precipitation polymerization in aqueous medium using an ammonium persulphate — potassium pyrosulphite redox initiator, was dried under reduced pressure at 40° C and ground to fine powder. The powder was dispersed in the ratio 1:12.5 /by weight/ in 70% colorless nitric acid cooled to −42° C, with 0.1% of urea previously added. The dispersion was stirred without cooling until its temperature increased to 18° C. The highly viscous polyacrylonitrile solution was then left standing at 18° C for 120 hours, actinic light being excluded. The solution was briefly degassed and extruded through a circular nozzle /FIG. 1a/, 1, provided with an axial inlet 2 for water, into a 2 m long horizontal coagulation bath, fresh water being introduced at the distant end, diluted nitric acid being removed by an overflow near the extrusion die. The coagulated tube was drawn off at a rate of 6 m per hour. The axial inlet was fed with water at a pressure of 15 cm water column. The washed tube had 4 inside diameter and 1 mm wall thickness. It contained 55% of water at swelling equilibrium.

From the same hydrogel solution a thick "monofil" was extruded without feeding water through the axial inlet. The thoroughly washed "monofil" had a 4 mm diameter, equal to the inside diameter of the tube. The tube previously made was then cut to 40 cm long pieces, the "monofil" to 1.5 cm long pieces which were then partially dried to about 20% water content. One end of the monofil was rounded on a grinder, the other cut in a 45° angle. The stopper thus obtained was partially swelled again in water so that it could be easily inserted into the end of the tube. Both the stopper and the tube end were then wetted with dimethyl sulphoxide, the stopper was slid into the tube and the whole left for 4 hours aside. Then a circular 4 mm hole was bored into the tube just above the stopper, the end of the tube rounded smooth and the catheter washed in luke-warm water until all dimethyl sulphoxide was removed. The other end of the catheter was stopped and dipped into a self-vulcanizing rubber latex in a length which is supposed to be exposed to the atmosphere when the catheter is applied to a patient. The dipping was repeated until a sufficiently thick rubber layer was obtained. The remaining part of the catheter was immersed overnight in a mixture of 75 p. of glycerol with 25 p. of water, wiped off and immersed for one minute into a 85° C warm concentrated sulphuric acid. The catheter was then briefly rinsed in water, immersed for 5 minutes in a surplus of a diluted sodium bicarbonate solution and washed in water again. After having been sterilized with ethylene oxide the catheter was packed in a sterile polypropylene foil packing containing 20 ml of sterile physiologic saline and sealed gas-tightly. The physiologic saline may contain, optionally, a suitable anaesthetic such as hydrochloride of diethylaminoethyl p-aminobenzoate and a bactericide. The catheter was of the "one use" type, but it could be also reused, if needed, and sterilized again at temperatures up to 100° C, using chemical sterilizing agents.

EXAMPLE 2

160 p. of acrylonitrile were dissolved in 837 p. of colorless 65% nitric acid. 1.2 p. of urea, dissolved in 2 p. of water, was added. After perfect dissolution of the colloidal urea nitrate the solution was initiated with 1 p.

of a 10% ammonium persulphate aqueous solution and sucked into a 1000 ml pipette, provided with a ground joint and tightly stoppered. The pipette was left standing for 72 hours at 22° C in darkness and then for 240 hours in a refrigerator at 10° C. The highly viscous solution was then extruded at room temperature through an extrusion die provided with an axial inlet for water. The polymer solution was extruded by means of carbon dioxide from a pressure bottle at 5 atm. gauge. The extruded tube was drawn off through an aqueous coagulation bath like in Example 1. The drawing off velocity and the feed of water through the axial inlet were adjusted so as to obtain a coagulated and washed tube with 3.2 inside diameter and 0.85 wall thickness. Its material — a multi-block copolymer of acrylonitrile with acrylamide — contained 58% of water at swelling equilibrium and displayed elastomeric characteristics. One end of the tube was filled with the same polymer solution by sucking it into the inclined tube. The tube end was then rapidly coagulated in water, neutralized in a diluted sodium bicarbonate solution and washed in water. The coagulated solution formed a stopper, firmly bound with the tube. The end was then rounded by grinding in half-dry condition, and a 3.2 mm opening was bored in the tube at the point where the stopper was nearest to the tube end. After new swelling in water and wiping the surface with filtering paper the other end of the tube was stoppered and the catheter was immersed in a mixture of 75 p. of glycerol and 25 p. of water for 9 hours in its whole length. Then the surface was wiped off and the catheter immersed, with its rounded end down, into 96% sulphuric acid at 23° C in a length of 20 cm. The treatment lasted 40 minutes. The acid was then rinsed off and the catheter neutralized in a surplus of a 1% aqueous sodium bicarbonate solution. The part not treated with the acid was immersed again in 75% glycerol for 12 hours, the surface wiped off and dipped repeatedly in a 10% polyvinyl acetate solution in acetone. The uppermost layer was obtained by dipping in a self-vulcanizing rubber latex and drying at 85° C. The catheter was sterilized and gas-tightly sealed in a polyethylene foil package containing 20 ml of physiological saline, containing, if desired, drugs according to a physicians prescription. In application to a patient the part introduced into urethra was very smooth and slippery, while the remaining part exposed to the atmosphere was permanently elastic and non-slippery so that it could be easily fixed with an adhesive tape. Its properties remain unchanged during a several weeks lasting application.

EXAMPLE 3

Using the method described in Example 2, a hydrogel tube was prepared having 4mm inside diameter and 0.3 mm wall thickness. The tube was swelled in a 65% dimethyl sulphoxide, the rest being water, at 60° c, and slipped onto a 5 mm thick catheter from plasticized PVC. The hydrogel tube overlapped the end of the catheter by about 15 mm and reached 25 cm from the end. The overlapping end, containing still dimethyl sulphoxide, was then heat-softened and pressed into a hot matrix bored in polytetrafluoroethylene. Dimethyl sulphoxide was then washed out in luke-warm water whereby the hydrogel tube shrank and adhered firmly to the PVC catheter. The surface was then treated for 45 seconds with a 30% sodium lye and thoroughly washed, then sterilized and packaged as described in foregoing Examples.

EXAMPLE 4

Figure 2:
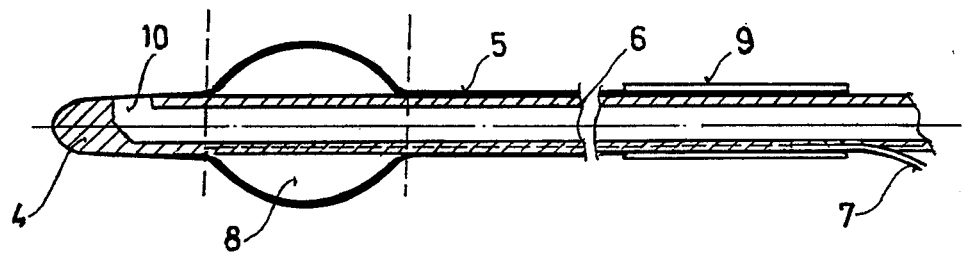
FIG. 2 is an axial section of a catheter according to Example 4.

A hydrogel tube was prepared in the way disclosed in Example 2, using, however, an extrusion die adjusted to form coagulated tube having the wall thicker at one side and provided with an axial groove 3 /FIG. 1b/. The catheter as a whole is diagrammatically illustrated in FIG. 2. Its end 4 was dipped into a hydrogel solution and shaped according to Example 2 in such a way that the groove 3 was filled with the gel up to 10 mm above the stopper. Further 30 mm of the tube surface were coated with an aqueous solution of sodium salt of carboxymethyl cellulose. A thin hydrogel tube 5 swelled in dimethyl sulphoxide diluted with 3% of water was slipped onto the main tube and left aside for 4 hours. The overlapping end was molded as described in Example 3 and the whole washed thoroughly in water. The outer tube 5 adhered firmly to the main tube 6. A thin rubber tubing 7 was inserted into the upper end of the axial groove 3 and fixed thereto. After annexing a rubber check valve to the rubber tubing 7 and washing the carboxymethyl cellulose salt out from the part forming the pocket, the pocket 8 could be inflated with physiological saline. The treatment with a 100° C hot mixture of 4 p. of concentrated sulphuric acid with 1 p. of glycerol for 15 seconds, neutralizing and washing made the catheter surface slippery in a desired length. The remaining part 9 of the catheter was covered with a sleeve from silicone rubber, swelled previously in toluene. After evaporating toluene the sleeve adhered firmly to the catheter, protecting in against drying. After having bored or cut the opening 10 the catheter was sterilized and packaged according to Example 1.

EXAMPLE 5

A catheter was made according to Example 2 except that the part to be exposed to the air was manufactured entirely from plasticized PVC and inserted with its tapering end into the hydrogel main tube, the outer hydrogel thin tube described in Example 4 being slid onto the main tube in a length overlapping the joint of the two parts of the catheter.

EXAMPLE 6

Surgical tubular device of the invention can be also manufactured by polymerization casting under cross-linking conditions: A mold illustrated diagrammatically in FIG. 3, consisted of two about 40cm long glass tubes 11 and 12, the outer one with 6 mm inside diameter, the inner one with 4 mm outer diameter. The tubes were assembled coaxially by means of two stoppers 13 and 14 provided with holes for filling and deaeration. The polyethylene stopper 14 formed simultaneously a filling funnel. The inserted end 15 of the tube 12 was sealed round and the end 16 of the tube 11 was closed with a silicone rubber stopper 17 hollowed out to mold the rounded end of the casting. The mold was precooled to −30° C and quickly filled up with an equally cooled mixture of 72 p. of a 70 % aqueous zinc chloride solution and 27 p. of anhydrous acrylonitrile. The cool mixture was initiated immediately before filling into the mold by adding 0.5 p. of a 5% aqueous potassium pyrosulphite and 0.5 p. of aqueous ammonium persulphate solutions and stirring thoroughly, while cooling from outside with an ethanol bath to which solid carbon dioxide was gradually added so as to keep the bath temperature at about −25° to about −35° C. The filled mold was then put into a freezer at −30° C. The zinc chloride solution contained a sufficient amount of ferric chloride so that the polymerization proceeded rather rapidly even at low temperatures. After 6 hours in the refrigerator the mold was taken out and left standing at room temperature for further 2 hours. Then the inner glass tube 12 was pulled out, stoppers 14 and 17 removed and the strong rubbery tube from plasticized polyacrylonitrile was pulled out using a double hook from a thick steel wire, catching the stopper 13 polymerized in the rubbery gel. The removal of the rubbery polymer casting was comparatively easy due to its high elasticity and strength. The end with the stopper 13 was cut off, a hole was cut at the closed end and the molding was then hanged on the lid of a tall glass beaker with 200 ml of concentrated hydrochloric acid poured on its bottom. A slow stream of hydrogen chloride, diluted with 90% of nitrogen, was led slowly through the molding from a capillary tube. After 36 hours at 18° C the partial hydrolysis was finished. The molding was immersed into a 0.5% sodium bicarbonate aqueous solution, hanging from the lid of another tall beaker. The precipitated white voluminous sediment was periodically sucked off from the bottom and replaced with the same volume of fresh bicarbonate solution. When no further precipitate was formed, the molding was washed first in diluted nitric acid and then in water to neutral reaction. The molding was transparent, pliable and elastic in swelled condition. Its outer diameter was 5 mm. The open end was stoppered and a thin rubber sleeve with 4.5 outside diameter was swelled in benzene so as to be easily slid on the catheter in a length of about 10 cm. After evaporating benzene the rubber sleeve shrank and adhered firmly to the catheter. The remaining part with the rounded end was dried to a 20% water content and immersed for 10 seconds into 50° C warm fuming sulphuric acid, rinsed with water and neutralized with a diluted sodium bicarbonate solution. After washing to neutrality the catheter swelled again with water and was sterilized and packaged as described in foregoing Examples.

EXAMPLE 7

8 p. of anhydrous acrylonitrile and 8 p. of crystalline acrylamide were dissolved in 84 p. of a mixture, consisting of 3 volume p. of 70% aqueous zinc chloride solution and 2 p. of saturated aqueous calcium chloride solution. The mixture was initiated with 0.15 % of potassium pyrosulphite and the same amount of ammonium persulphate, related to the sum of the two monomers. The solution was then stirred under carbon dioxide for 6 hours. Thereafter a half portion of the same redox initiator was added and the stirring was continued at ambient temperature for further 4 hours. The viscous solution thus obtained was deaerated using a water jet pump and extruded using the extrusion die described in Example 1. Wash waters were precipitated with sodium bicarbonate and the precipitate utilized for the recovery of zinc chloride. The tube was cut to pieces of an appropriate length, a stopper from the same hydrogel was cemented into one end of each tube, using a 10% solution of the same hydrogel in dimethyl sulphoxide. The catheter was put aside for 3 hours, dimethyl sulphoxide washed out in water, the catheter dried to a content of 20% water and the end rounded. An opening was bored just above the stopper, the catheter swelled in water to equilibrium and two thirds of its length were immersed for 40 seconds in an 80° C warm mixture of 4 p. concentrated sulphuric acid with 1 p. of anhydrous ethylene glycol. The acid was then rinsed off with a stream of tap water and the catheter neutralized in a surplus of a diluted sodium bicarbonate solution. The remaining one third of its length was then covered with a thin rubber sleeve as described in Example 6. Prior to the partial coating with the rubber sleeve the catheter was immersed for 30 minutes into an 80° C warm aqueous solution of 0.5 % of formaldehyde and 0.5 % of concentrated hydrochloric acid and then washed thoroughly in water. The catheter was wiped with filtering paper and left for 30 minutes in the air at ambient temperature. Then it was immersed for 30 seconds into a 80° C warm mixture of sulphuric acid and glycerol 1:4, rinsed, neutralized, washed, sterilized and packaged as described in Example 1.

EXAMPLE 8

The process described in Example 3 was repeated with the only difference that the outer thin tube was cemented to the main tube at the two ends only in a length of about 15 mm. Thus, the space between the hydrogel tubes could be filled with physiologic saline containing drugs, if desired. The outer thin tube was thereby slightly pressed against the uretha closing the latter tightly. The end protruding into the bladder was simultaneously inflated.

EXAMPLE 9

Figure 4:
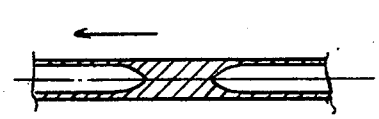
FIG. 4 is an axial section through the extruded tube at the point where the feeding of the coagulating bath through the axial inlet of the die was temporarily interrupted and the feed of the polymer solution simultaneously increased to keep the outer diameter unchanged.

The hydrogel tube was formed by extrusion according to Example 1, interrupting, however, the water inlet into the axial mandrel periodically in about 90 cm intervals and increasing simultaneously the rate of extrusion so that a hydrogel stick with full cross section was formed between two closed endings as shown in FIG. 4 in an axial section. The tubes as well as the sticks between them were cut in the middle so that the ends could be rounded and bored in half-dry condition. The dead space in the end could be removed either by inserting a bevelled stopper and cementing it to the interior of the tube end, or by introducing a suitable amount of a highly viscous hydrogel solution through the side opening and coagulating and washing it in water.

In the same way thin tubes, closed at one end, can be made, to be slipped onto the main tube or onto a ready made catheter.

EXAMPLE 10

Figure 3:
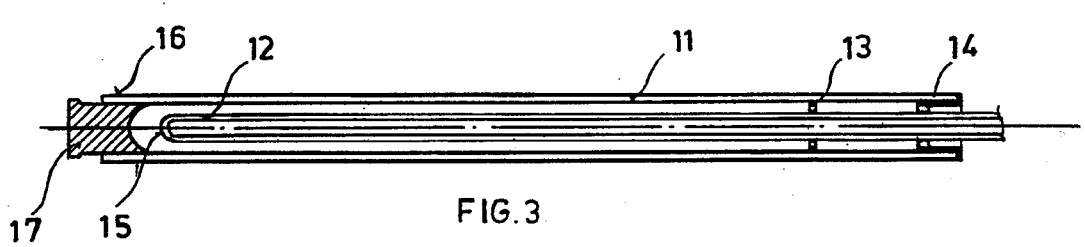
FIG. 3 illustrates a glass mold described in Example 5, employed for polymerization-casting under cross-linking conditions.

A mold like that illustrated in FIG. 3 was made from polytetrafluoroethylene in such a way that the outer tube was assembled of two exactly fitting longitudinal halves clamped tightly together. The end of the inner tube was bevelled so as to exclude dead space at the opening. The mold was filled with a homogeneous mixture of 30 p. of acrylonitrile, 69 p. of 65% nitric acid, 0.2 p. of urea, 0.6 p. of potassium persulphate, 1 p. of acetylacetone and 0.002 p. of ferric nitrate, precooled to 0° C. The filled mold was kept at −1° C for 24 hours, then left standing at room temperature for 6 hours, heated for one hour to 30° C and then left standing for 300 hours at 14° C. The mold was then dismantled, the molding, with the inner tube still in, washed in water to neutral reaction and the inner tube pulled out. A 3.5 mm hole was cut at the end using a circular knife, the catheter left for 30 minutes in the air to get the surface almost dry, and then it was exposed to diluted vapors of chlorosulphonic acid for two minutes. Neutralizing, washing, sterilizing followed. The part supposed to protrude in the air during the application to a patient was covered with a thin rubber sleeve as described in Example 6.

EXAMPLE 11

12 p. of acrylonitrile were dissolved in 88 p. of a mixture of 70% aqueous zinc chloride solution and saturated calcium chloride solution, volume ratio 3:2, the mixture was cooled to −10° C, whereafter 0.015 p. of potassium pyrosulphite and 0.02 p. of ammonium persulphate were stirred in. The polymerizing mixture was cooled while stirring under inert gas so that the temperature did not exceed 20° C. Zinc chloride solution contained a sufficient amount of catalytically active impurities, particularly iron and titanium compounds, so that it was not necessary to add ferric or cupric salts as usual. The very viscous solution thus obtained was heated to 80° C and dearated. It was then extruded as described in Example 1 into a coagulation bath containing 45 % of zinc and calcium chlorides in the same ratio as used in the polymerization step. The concentration of the salts was kept constant by adding water countercurrently and removing the bath gradually near the extrusion die. The coagulated tube was drawn off with such a velocity that a tube with desired inside and outside diameter was obtained, and the path length in the bath was chosen so as to obtain a rubbery salt plasticized polyacrylonitrile containing about 30% of the polymer. The rubber-like transparent tube was wiped off between two rollers coated with foamed rubber and cut to about 40 cm long pieces. The tubes were flushed with dry air to remove the remaining bath from their interior and hung with their ends into the holes of a perforated plate, leaving the passage through the tubes free. The perforated plate formed a horizontal partition of a 20 liters PVC container filled with nitrogen containing 5 % of hydrogen chloride and 0.2 % of formaldehyde. The gas circulated by means of a by-pass and a small circulating pump through and around the gel tubes. The partial hydrolysis lasted 24 hours at 19° C. The tubes were washed ten times in a diluted aqueous sodium bicarbonate solution and finally in distilled water. Further treatment followed according to Example 1.

Similar rubbery tubes plasticized with zinc chloride solution can be obtained by partially coagulating the polyacrylonitrile solution in plain water so that a coagulated skin covers a core containing uncoagulated viscous solution. After several hours at room temperature the concentration of zinc chloride becomes uniform throughout the whole cross section due to diffusion. Thus all what is needed is to increase the polymer concentration to about 25–35 % and to leave the tube until the zinc chloride concentration is equalized. The temperature and time of the partial hydrolysis with hydrogen chloride, as well as the concentration of the latter are adjusted so as to obtain uniformly hydrolyzed polymer.

Figure 5:
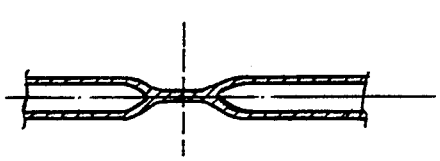
FIG. 5 is an axial section of an extruded tube at the point where the feed of the coagulating liquid through the axial mandrel was entirely interrupted, the feed of the polymer solution being simultaneously throttled, as described in Example 11.

Instead of using a gel stopper it is possible also to stop periodically the water inlet into the axial mandrel of the extrusion die and to throttle simultaneously the feed of the polymer solution so that the tube closes periodically closed as shown in FIG. 5.

EXAMPLE 12

150 p. of anhydrous acrylonitrile were dissolved in 846 p. of 65% colorless nitric acid, and 1.2 p. of urea, dissolved in 2 p. of water, was stirred therein. The solution was cooled down to −5° C and the polymerization started by addition of 1 p. of a 10% aqueous solution of ammonium persulphate and 1 p. of acetyl acetone and 0.001 p. of ferric nitrate. The solution was kept at 0° C for 24 hours, left standing overnight at room temperature and heated while stirring slowly to 30° C for 2 hours. Thereafter the highly viscous solution was left standing for 300 hours at 10° C. The highly viscous solution was then extruded as described in Example 2, except that the not yet fully coagulated tube near the extrusion die was led through a device illustrated in FIG. 6, consisting of a hollow ring 18, the inner wall of which was formed by a rubber tue 19 inflated periodically by leading compressed air into the hollow ring 18. The device moved, when inflated, along a short path with the tube, returning when deflated into the starting position. The effect was similar to that shown in FIG. 5. The washed tube was cut to individual catheters which were then made slippery by introducing anionic neutralized groups into the surface layer and provided with a rubber sleeve as described in foregoing Examples.

We claim:
1. A surgical tubular device to be introduced temporarily into cavities of a living body such as a catheter, intubation or sounding tube, cystoscope or the like, comprising an insertion end including a surface area extending therefrom consisting essentially of a hydrophilic polymer of acrylonitrile and a hydrophilic comonomer selected from the group consisting of acrylonitrile, acrylamide, acrylic acid, methacrylamide, methacrylic acid, ethylene sulphonic acid and their salts, said polymer being swelled with an aqueous liquid, and containing neutralized anionic groups making it highly slippery in contact with water, and an opposite end having a surface area extending backward therefrom to be exposed to the atmosphere during use being protected against drying by a layer of an elastic polymer or copolymer impermeable to water and water vapors.

2. Surgical tubular device according to claim 1, wherein the hydrophilic polymer is a multi-block polymer containing in each macromolecule several sequences of acrylonitrile units separated by sequences of acrylamide or acrylic acid units.

3. Surgical tubular device according to claim 1, wherein the said anionic groups are selected from the group consisting of carboxylic, sulphonic, sulphuric and phosphoric acid side substituents.

4. Surgical tubular device according to claim 1, wherein at least the insertion end includes an outer layer consisting of an uninterrupted thin tube of said hydrophilic polymer, overlying an elastic inner tube.

5. Surgical tubular device according to claim 4, wherein the thin outer tube is partially cemented to said inner tube, the loose part forming an inflatable pocket connected by a passage means with and exposed to the atmosphere when said device is in use.

6. Surgical tubular device according to claim 5, wherein said passage means is formed by a longitudinal groove in the surface of the inner tube, covered by the said thin outer layer.

* * * * *